US00PP24798P2

(12) United States Plant Patent
de Bruijn

(10) Patent No.: US PP24,798 P2
(45) Date of Patent: Aug. 19, 2014

(54) ***ASTILBE* PLANT NAMED 'LOOK AT ME'**

(50) Latin Name: *Astilbe arendsii*
Varietal Denomination: Look at Me

(71) Applicant: Tom de Bruijn, 's Gravenzande (NL)

(72) Inventor: Tom de Bruijn, 's Gravenzande (NL)

( * ) Notice: Subject to any disclaimer, the term of this patent is extended or adjusted under 35 U.S.C. 154(b) by 0 days.

(21) Appl. No.: 13/694,819

(22) Filed: Jan. 7, 2013

(51) Int. Cl.
*A01H 5/00* (2006.01)

(52) U.S. Cl.
USPC ..... Plt./407

(58) Field of Classification Search
USPC ..... Plt./407
See application file for complete search history.

*Primary Examiner* — Anne Grunberg
(74) *Attorney, Agent, or Firm* — C. A. Whealy

(57) ABSTRACT

A new and distinct cultivar of *Astilbe* plant named 'Look at Me', characterized by its compact, broadly upright and mounding plant habit; dense and bushy appearance; freely and uniformly flowering habit; pink-colored flowers positioned just above the foliar plane on strong and sturdy red-colored peduncles; and good container and garden performance.

3 Drawing Sheets

Botanical designation: *Astilbe arendsii.*
Cultivar denomination: 'LOOK AT ME'.

BACKGROUND OF THE INVENTION

The present invention relates to a new and distinct cultivar of *Astilbe*, botanically known as *Astilbe arendsii* and hereinafter referred to by the name 'Look at Me'.

The new *Astilbe* plant is a product of a planned breeding program conducted by the Inventor in 's Gravenzande, The Netherlands. The objective of the breeding program was to create new uniform and freely flowering *Astilbe* plants with attractive leaf and flower coloration.

The new *Astilbe* plant originated from a cross-pollination made by the Inventor in 2003 in 's Gravenzande, The Netherlands, of two unnamed *Astilbe arendsii* seedling selections, not patented. The new *Astilbe* plant was discovered and selected by the Inventor as a single flowering plant from within the progeny of the stated cross-pollination in a controlled greenhouse environment in 's Gravenzande, The Netherlands in 2005.

Asexual reproduction of the new *Astilbe* plant by vegetative divisions in a controlled environment in Afferden, The Netherlands since 2005 has shown that the unique features of this new *Astilbe* plant are stable and reproduced true to type in successive generations.

SUMMARY OF THE INVENTION

Plants of the new *Astilbe* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Look at Me'. These characteristics in combination distinguish 'Look at Me' as a new and distinct *Astilbe* plant:

1. Compact, broadly upright and mounding plant habit.
2. Dense and bushy appearance.

3. Freely and uniformly flowering habit.
4. Pink-colored flowers positioned just above the foliar plane on strong and sturdy red-colored peduncles.
5. Good container and garden performance.

Plants of the new *Astilbe* differ primarily from plants of the parent selections in the following characteristics:

1. Plants of the new *Astilbe* are more compact than plants of the parent selections.
2. Plants of the new *Astilbe* are more freely flowering than plants of the parent selections.
3. Plants of the new *Astilbe* have stronger and sturdier stems, peduncles and pedicels than plants of the parent selections.

Plants of the new *Astilbe* can be compared to plants of *Astilbe arendsii* 'Gloria', not patented. In side-by-side comparisons conducted in Afferden, The Netherlands, plants of the new *Astilbe* and 'Gloria' differed in the following characteristics:

1. Plants of the new *Astilbe* were more compact than plants of 'Gloria'.
2. Plants of the new *Astilbe* were denser and bushier than plants of 'Gloria'.
3. Plants of the new *Astilbe* were more freely flowering than plants of 'Gloria'.
4. Inflorescences of plants of the new *Astilbe* and 'Gloria' differed in peduncle and pedicel color as plants of 'Gloria' had green-colored peduncles and pedicels.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet comprises a side perspective view of a typical flowering plant of 'Look at Me' grown in an outdoor nursery.

The photograph on the second sheet is a close-up view of a typical developing inflorescence of 'Look at Me'.

The photograph on the third sheet is a close-up view of fully developed inflorescences of 'Look at Me'.

DETAILED BOTANICAL DESCRIPTION

The aforementioned photographs and following observations, measurements and values describe plants grown during the late summer/early autumn in an outdoor nursery in Afferden, The Netherlands and under cultural practices typical of commercial *Astilbe* production. During the production of the plants, day temperatures ranged from 16° C. to 32° C. and night temperatures ranged from 6° C. to 18° C. Plants were one year old when the photographs and description were taken. In the following description, color references are made to The Royal Horticultural Society Colour Chart, 2007 Edition, except where general terms of ordinary dictionary significance are used.

Botanical classification: *Astilbe arendsii* 'Look at Me'.

Parentage:

*Female, or seed, parent*.—Unnamed *Astilbe arendsii* seedling selection, not patented.

*Male, or pollen, parent*.—Unnamed *Astilbe arendsii* seedling selection, not patented.

Propagation:

*Type*.—By divisions.

*Time to initiate roots*.—About three weeks at temperatures about 20° C.

*Root description*.—Thick, fleshy; brown and white in color.

*Rooting habit*.—Freely branching; dense.

Plant description:

*Plant form and growth habit*.—Herbaceous perennial; compact, broadly upright and mounding plant form with inflorescences held just above the foliar plane; flowering stems and leaves basal; freely flowering with numerous basal branches developing per plant, dense and bushy appearance; low vigor to moderately vigorous growth habit; freely and uniformly flowering habit.

*Growth rate*.—Moderate to slow; from divisions, about ten months are required to produce fully-grown flowering plants in containers.

*Plant height* (*soil level to top of foliar plane*).—About 19 cm.

*Plant height* (*soil level to top of inflorescences*).—About 44 cm.

*Plant width* (*spread*).—About 40.5 cm.

*Stem description*.—Length: About 13.3 cm. Diameter: About 3 mm. Strength: Strong, sturdy. Texture: Sparsely pubescent. Color: Close to 165B; towards the base, close to 172A.

Foliage description:

*Arrangement*.—Alternate in basal rosettes; biternately compound; about 21 leaflets per leaf.

*Leaf length* (*excluding petiole*).—About 15.9 cm.

*Leaf width*.—About 18.4 cm.

*Terminal leaflet length*.—About 5.6 cm.

*Terminal leaflet width*.—About 2.8 cm.

*Lateral leaflet length*.—About 4 cm.

*Lateral leaflet width*.—About 2.1 cm.

*Leaf shape*.—Roughly deltoid to broadly ovate in outline.

*Lateral and terminal leaflet shape*.—Elliptic to narrowly ovate.

*Lateral and terminal leaflet apex*.—Acute.

*Lateral and terminal leaflet base*.—Rounded to cuneate.

*Lateral and terminal leaflet margin*.—Biserrate.

*Lateral and terminal leaflet texture, upper and lower surfaces*.—Moderately pubescent; rough.

*Lateral and terminal leaflet venation pattern*.—Pinnate.

*Lateral and terminal leaflet color*.—Developing leaflets, upper surface: Close to 143A to 143B. Developing leaflets, lower surface: Close to 143B to 143C. Fully expanded leaflets, upper surface: Between N137A and 147A; venation, close to 148C. Fully expanded leaflets, lower surface: Close to 147B; venation, close to 174C to 174D.

*Leaf petiole length*.—About 8.9 cm.

*Leaf petiole diameter*.—About 1 mm.

*Leaflet petiole length*.—About 1.4 cm.

*Leaflet petiole width*.—About 0.75 mm.

*Leaf and leaflet petiole texture, upper and lower surfaces*.—Smooth, glabrous.

*Leaf and leaflet petiole color, upper surface*.—Close to 178A.

*Leaf and leaflet petiole color, lower surface*.—Close to 145B to 145C.

Flower description:

*Flower type and flowering habit*.—Single rotate flowers arrange on terminal panicles; flowers face upright, outwardly or drooping depending on position on the inflorescence; racemes roughly conical in shape; freely and uniformly flowering habit with about 750 flowers per inflorescence.

*Fragrance*.—Moderately strong; sweet, pleasant. Natural flowering season: Plants begin flowering about ten months after planting; continuously flowering from early to late summer in The Netherlands.

*Postproduction longevity*.—Flowers last about ten days on the plant; flowers persistent.

*Flower buds*.—Height: About 3 mm. Diameter: About 2 mm. Shape: Ovoid. Color: Close to 69D; towards the apex, close to 70C.

*Inflorescence height*.—About 21.1 cm.

*Inflorescence diameter*.—About 9.3 cm.

*Flower diameter*.—About 5 mm.

*Flower depth*.—About 4 mm.

*Petals*.—Quantity per flower: Typically five in a single whorl. Length: About 3 mm. Lobe width: About 1 mm. Shape: Oblanceolate. Apex: Broadly acute. Margin: Entire. Texture, upper and lower surfaces: Smooth, glabrous. Color: Developing petals, upper and lower surfaces: Close to NN155C. Fully expanded petals, upper and lower surfaces: Close to NN155C.

*Sepals*.—Quantity per flower: Typically five in a single whorl, fused towards the base; campanulate-shaped calyx. Length: About 2 mm. Width: About 0.75 mm. Shape: Ovate. Apex: Acute. Margin: Entire. Texture, upper and lower surfaces: Smooth, glabrous. Color: Developing sepals, upper and lower surfaces: Close to 70C; towards the base, close to 69D. Fully expanded sepals, upper and lower surfaces: Close to 70C; towards the base, close to 69D.

*Peduncles*.—Length: About 20.7 cm. Diameter: About 2.5 mm. Angle: Erect to about 40° from vertical.

Strength: Strong, sturdy. Texture: Smooth, glabrous. Color: Close to 53B to 53D.

*Pedicels*.—Length: About 1 mm. Diameter: About 0.5 mm. Angle: About 50° from peduncle axis. Strength: Strong, sturdy. Texture: Smooth, glabrous. Color: Between 53D and 54A.

*Reproductive organs*.—Stamens: Quantity per flower: Typically ten. Filament length: About 2 mm. Filament color: Close to 56D; towards the base, close to 55B. Anther shape: Ovate, basifixed. Anther length: About 0.2 mm. Anther color: Close to 158D. Pollen amount: Scarce. Pollen color: Close to N155A. Pistils: Quantity per flower: Typically two. Pistil length: About 1.5 mm. Stigma shape: Club-shaped. Stigma color: Close to 56A. Style length: About 1.3 mm. Style color: Close to 56D. Ovary color: Close to 155A.

*Seeds and fruits*.—Seed and fruit development have not been observed on plants of the new *Astilbe*.

Disease & pest resistance: Plants of the new *Astilbe* have not been noted to be resistant to pathogens and pests common to *Astilbe* plants.

Garden performance: Plants of the new *Astilbe* have been observed to have good garden performance and tolerate rain, wind and high temperatures of about 35° C. Plants of the new *Astilbe* have been observed to be hardy to USDA Hardiness Zone 5.

It is claimed:

1. A new and distinct *Astilbe* plant named 'Look at Me' as illustrated and described.

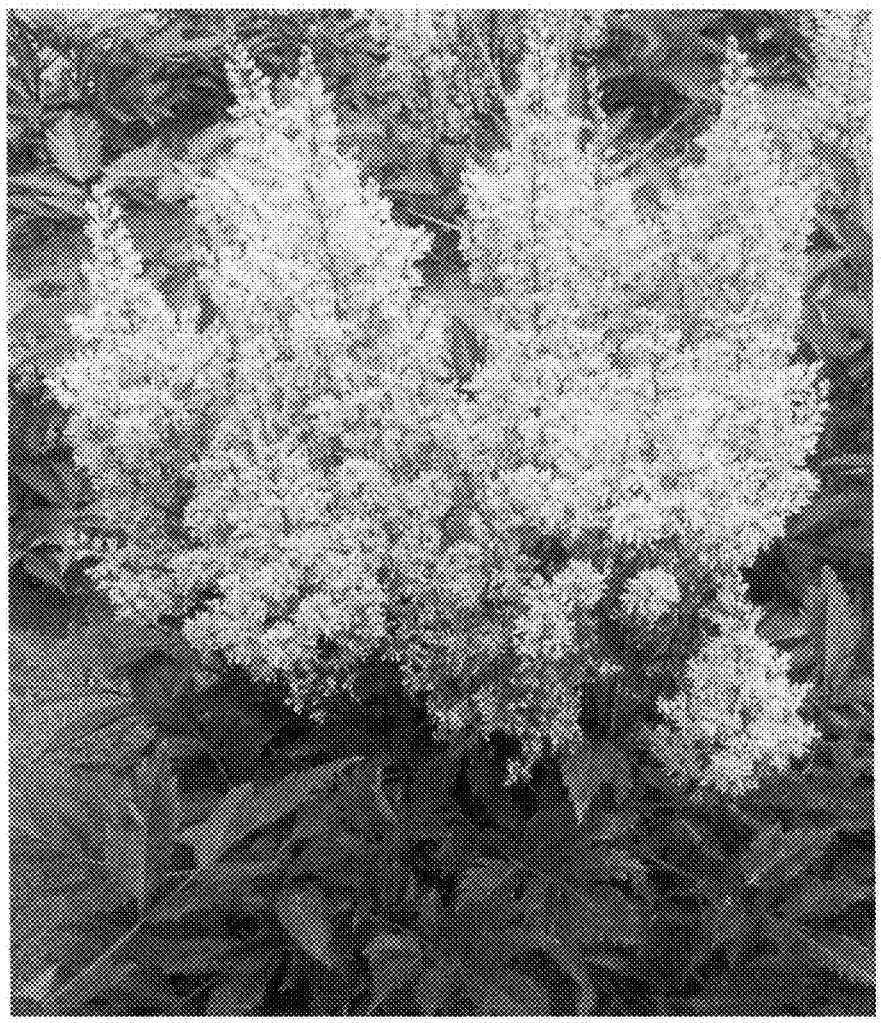

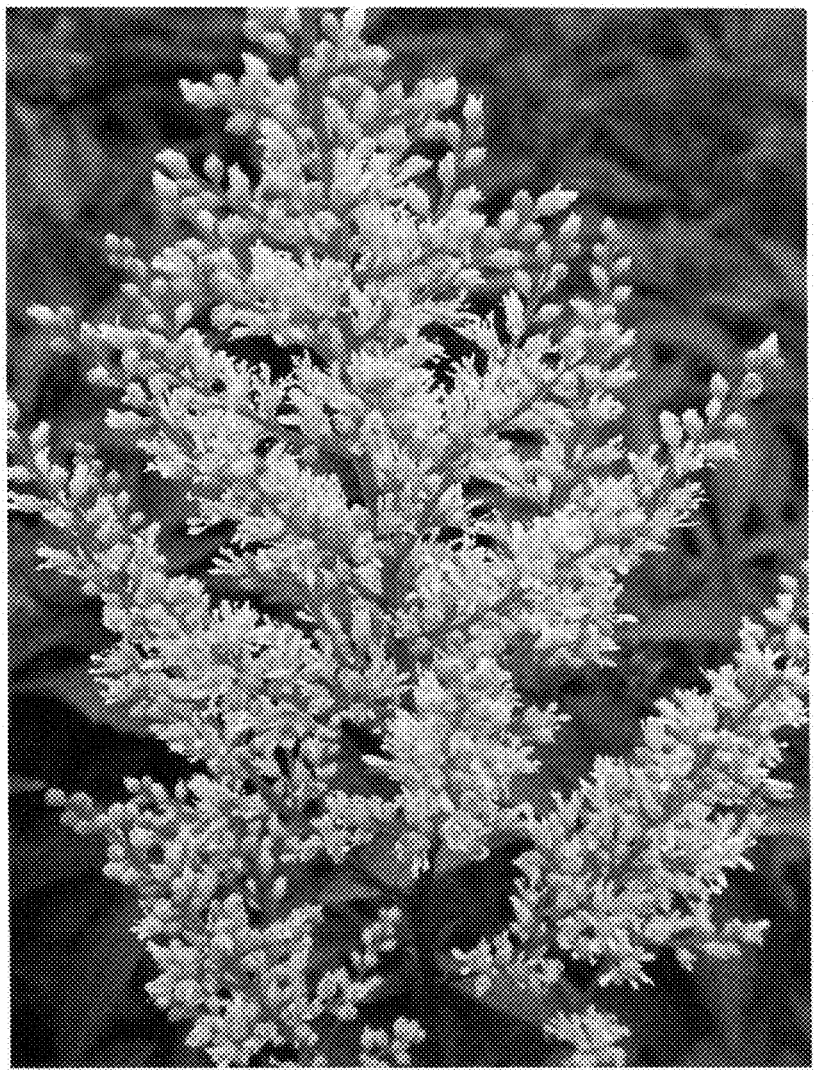

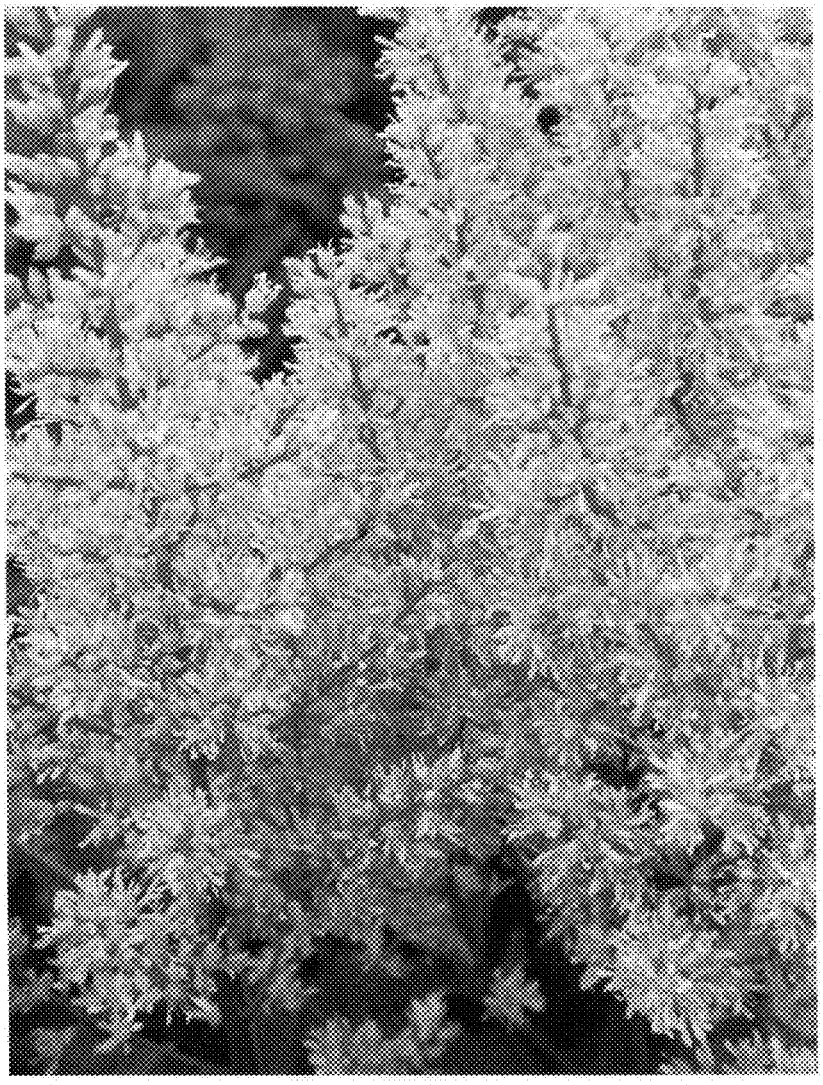

* * * * *